United States Patent [19]

Hiratani et al.

[11] Patent Number: 5,173,415
[45] Date of Patent: Dec. 22, 1992

[54] PROCESS FOR REMOVAL OF VIRUSES FROM SOLUTIONS OF PHYSIOLOGICALLY ACTIVE SUBSTANCES

[75] Inventors: Hajime Hiratani, Sennan; Jun Tateishi; Tetsuyuki Kitamoto, both of Fukuoka, all of Japan

[73] Assignee: Japan Chemical Research Co., Ltd., Kobe, Japan

[21] Appl. No.: 640,569

[22] Filed: Jan. 14, 1991

Related U.S. Application Data

[63] Continuation of Ser. No. 344,521, Apr. 21, 1989, abandoned, which is a continuation of Ser. No. 937,605, Dec. 3, 1986, abandoned.

[30] Foreign Application Priority Data

Jan. 20, 1986 [JP]  Japan ................................. 61-9811

[51] Int. Cl.$^5$ .................... C12N 9/00; C12N 9/08; C12N 9/72; C07K 3/26
[52] U.S. Cl. .................................... 435/183; 435/192; 435/215; 435/217; 530/344; 530/414
[58] Field of Search .............. 435/183, 187, 192, 215, 435/217; 530/300, 344, 350, 412, 414, 427, 827-854

[56] References Cited

U.S. PATENT DOCUMENTS

| | | | |
|---|---|---|---|
| 4,663,227 | 5/1987 | Yamamori et al. | 428/315.7 |
| 4,711,793 | 12/1987 | Ostreicher et al. | 427/244 |
| 5,076,933 | 12/1991 | Glenn et al. | 210/641 |

OTHER PUBLICATIONS

Cliver, "Factors in the Membrane Filtration of Enteroviruses", Applied Microbiology 13(3):417–425 (May 1965).
Maniatis et al., Molecular Cloning—A Laboratory Manual CSH 1982 pp. 325–326.
Bowen et al., Nucleic Acids Research vol. 8, #11980, pp. 1–20.

*Primary Examiner*—Richard A. Schwartz
*Assistant Examiner*—Michelle L. Johnson
*Attorney, Agent, or Firm*—Burgess, Ryan and Wayne

[57] ABSTRACT

A membrane filter of 0.025 to 0.05 $\mu$ in pore size is treated by passing the solution of a water-soluble high molecular substance such as albumin, dextran, polyvinylpyrrolidone, polysorbate 80, gelatin or the like through the membrane filter. Employing the filter thus treated, the solution of a physiologically active substance of human origin such as human growth hormone, kallikrein, trypsin inhibitor, epidermal growth factor, leucocyte interferon etc. is filtered at high recovery rate of the active substance avoiding the adsorption of the active substance onto the filter. By the filtration, harmful viruses such as Creutzfeldt-Jacob disease pathogen which may exist in the physiologically active substance can be removed.

3 Claims, No Drawings

PROCESS FOR REMOVAL OF VIRUSES FROM SOLUTIONS OF PHYSIOLOGICALLY ACTIVE SUBSTANCES

This application is a continuation of application Ser. No. 344,521, filed Apr. 21, 1989, now abandoned which is a 1.62 continuation application of U.S. Ser. No. 937,605, filed Dec. 3, 1986, now abandoned.

BACKGROUND OF THE INVENTION

1) Field of the Invention

The present invention relates to a process for removing possibility of mixing a harmful virus into a physiologically active substance originated from human urine, blood and internal organs in high recovery rate of the active substance.

2) Description of the Related Art

In recent years, it has been reported that a disease assumed to be Creutzfelt-Jacob disease (hereinafter referred to briefly as "CJD") occurred in eight patients with pituitary dwarfism in the United States of America and one case of the same disease in the United Kingdom who had been given preparations of human growth hormone produced from human pituitaries being employed as a starting material (Scrip No. 995, p. 25, 1985; The Lancet, Aug. 3, p. 244, 1985).

The causative factor of said CJD has not yet been identified up to now, but the slow virus is considered to cause the disease, with the incidence being regarded as about one per million persons.

The pathologic characteristic of CJD is that there are observed spongiform deformity in the cerebral cortex and degeneration in various nervous systems.

Using brain homogenates of the mice having developed CJD, inactivation of the virus was attempted by means of different methods by J. Tateishi, et al., Department of Neuropathology, Faculty of Medicine, Kyushu University, Japan (Annals of Neurology, 7 (4), 890-891 (1980); Gazette of Medical Society of Japan (*Nippon Ishikai Zasshi*), 84 (3), 275-282 (1980).

According to the above literature, the mouse brain homogenate containing the virus is not inactivated by either heat treatment (at 60° C. for 30 minutes; at 80° C. for 10 minutes; at 100° C. for 10 minutes), ultraviolet irradiation, one-year treatment with formalin (10%), one-week treatment with glutaraldehyde (2%), one-year treatment with sodium hypochloride (1%), one-year treatment with iodine (3%), one-year treatment with hydrogen peroxide (30%), 15-hour treatment with potassium permanganate (2 mM), 15-hour treatment with 95% ethanol, etc.

However, it was found that only filtration treatment with a membrane filter having 0.025μ of pore size and extraction with chloroform:ethanol (3:1) mixture were able to permit removal of the CJD virus, whereas filtration treatment with a membrane filter of an increased pore size as large as 0.10 failed to eliminate the CJD According to the literatures reported by Tateishi et al., CJD symptoms are developed by inoculating the cerebral cortex of CJD patient in highest probability as compared with other cases. However, there are records describing the development of CJD symptoms by inoculating other internal organs, blood or urine etc., which lead to the possibility that CJD virus may mix into a physiologically active substance produced by employing the above materials as starting materials.

Therefore, it is necessary to prevent the virus which exhibits a stubborn resistance to heat and medicines from mixing into the preparations of the physiologically active substance.

SUMMARY OF THE INVENTION

The present inventors have disclosed in Japanese Patent Application (No. 223060/1985) that, in a method wherein filtration with a membrane filter of 0.025μ in pore size is incorporated into a process of producing human growth hormone to remove CJD virus which might mix in the hormone, a process for recovering human growth hormone in high efficiency preventing the hormone from adsorbing onto a membrane filter by previously treating the membrane filter with human serum albumin.

Subsequently, pretreatment by other substances than human serum albumin have been researched. As a result, it was found that the same effect of preventing the adsorption as that of albumin was found and a more effective recovery rate was obtained by pretreating the membrane with the solution of polyvinylpyrrolidone, polyoxyethylene sorbitan mono-laurate, polysorbate 80, Poligeline (modified gelatin, Hochst, Japan), gelatin or the like.

With regard to low molecular dextran, arginine, polyethyleneglycol, polypropyleneglycol etc., the effect of preventing the adsorption was also studied, however, good results were not obtained.

As described above, these experiments were conducted with regard to human growth hormone originated from internal organs.

The research was developed to further similar experiments with regard to other physiologically active substances. Namely, with regard to a physiologically active substance orginated from human urine such as urokinase, kallikrein, trypsin inhibitor, epidermal growth factor, human placenta gonodotropin and hypophysis gonadotropin; a physiologically active substance originated from human blood such as interferon-α, interferon-γ, superoxide dismutase, plasminogen, antitumor factor originated from platelet etc., desired preventing effect of the adsoption was obtained by filtration through the membrane filter previously treated with the above-mentioned materials being able to prevent the adsorption.

DESCRIPTION OF THE PREFERRED EMBODIMENTS

The present invention is directed to a process for producing a physiologically active subtance of human origin which comprises filtering a solution of the active substance through a membrane filter of 0.025 to 0.05μ in pore size, the membrane filter being previously treated with a solution of a water-soluble high molecular substance which practically does not hinder the active substance from passing through the membrane filter.

The physiologically active substances of human origin include proteinaceous substances originated from human urine, human blood, human internal organs etc., as exemplified in the following:

The physiologically active substances originated from human urine are, for instance, urokinase, kallikrein, trypsin inhibitor, human epidermal growth factor, human placenta gonadotropin, hypophisis ganadotropin etc.

The physiologically active substances originated from human blood are, for instance, interferon-α, interferon-γ, superoxide dismutase, plasminogen and an antitumor factor of platelet origin.

The physiologically active substances originated from human internal organs are, for instance, a hormone such as human growth hormone etc.

These physiologically active substances of human origin are purified by a method consisting of many steps, for example, precipitation, adsorption onto and elution from an adsorbent or an ion-exchanger, and filtration. The process of present invention can be incorporated into a suitable step of the the method or can be added to the method as the final step.

As the membrane filter, there may be exemplified that having 0.025 to 0.05μ of pore size, which is available as a commercial product produced by Millipore Co. (Japan), Sartorius Co. (West Germany) and Nuclepore Co. (U.S.A.).

In this invention, the membrane filter is previously treated with a water-soluble high molecular substance which practically does not hinder the physiologically active substance from passing though the filter.

The phrase "practically does not hinder the solution of physiologically active substance from passing though the membrane filter" means that at least the major part of activity of the physiologically active substance is able to pass through the filter. It is desirable to recover at least about 80% of the activity in the filtrate, because the physiologically active substances of human origin are expensive in general.

As the water-soluble high molecular substance having the above-mentioned property, there may be exemplified human serum albumin, polyvinylpyrrolidone, polyoxyethylene sorbitan monolaurate such as Tween 20 (Nakarai Kagaku Co.), polysorbate 80 such as Tween 80 (ibid.), modified gelatin such as Poligeline (Hochst, Japan), gelatin etc.

The pretreatment of the membrane filter can be performed conveniently by passing an aqueous solution of the high molecular substance through the filter, whereby the substance is adsorbed onto the filter. The passing of the solution may be carried out by means of filtration, impregnation, soak etc. The concentration of the high molecular substance in the solution can be selected from wide range as far as the purpose of the pretreatment is not obstructed, however, employing a concentration from 0.2 to 0.5%, the purpose is sufficiently achieved in general.

The membrane filter which has been pretreated with a water-soluble high molecular substance is washed with water to remove excess of the substance.

With use of the thus treated filter, the solution of the physiologically active substance is subjected to filtration. The solution of the substance can be prepared in the form of an aqueous solution such as a solution in physiological saline. The purity and concentration of the physiologically active substance can be selected over such a range as may not impede the filtration through the specified membrane filter, but needless to say, an enhanced degree of purity of the substance facilitates the operation more easily.

By the above procedure, the solution of the physiologically active substance can be filtered through a membrane filter in improved yield.

In the present invention, the pretreatment of a membrane filter with a water-soluble substance prevents the adsorption of the physioligically active substance onto the filter in the subsequent filtration of the physiologically active substance, thereby rendering it possible to allow the physiologically active substance to pass through the membrane filter in improved yield. And the filtration enables the efficient removal of the CJD virus or other filterable viruses which may exist in the physiologically active substances of human origin.

The examples are described in the following to illustrate this invention in more detail, but this invention is not to be limited by them.

REFERENCE EXAMPLE 1

1. Experimental materials

| Pore size | Catalogue No. |
|---|---|
| Membrane filters produced by Millipore Co. of Japan: | |
| 0.01μ | (VSWP02500) |
| 0.050μ | (VMWP02500) |
| 0.10μ | (VCWP02500) |
| Membrane filters produced by Sartorius Co. of West Germany: | |
| 0.015μ | (11318) |
| 0.05μ | (11328) |
| 0.10μ | (11358) |
| Membrane filters produced by Nuclepore Co. of U.S.A.: | |
| 0.015μ | (110601) |
| 0.03μ | (110602) |
| 0.05μ | (110603) |
| 0.08μ | (110604) |

2. Experimental method

The following experiment was carried out with 80 ml (0.60 IU/ml) of a human growth hormone solution (a physiological saline solution):

Using a 10-ml disposable syringe, 7 ml of the human growth hormone solution for each filter was filtered through a filter of 25 cm in diameter being fixed onto a filter holder.

Throughout the experiment, each filter was autoclaved in advance (at 120° C. for 30 minutes), followed by passing 5 ml of physiological saline and the test solution (human growth hormone solution), successively, through each membrane.

The human growth hormone was quantitatively determined by radioimmunoassay (RIA Kit manufactured by Dalnabot Co.).

3. Experimental results

The results are shown in Table 1.

TABLE 1

| Membrane filter | Recovery (%) of HGH* activity in filtrate |
|---|---|
| Produced by Millipore Co. | |
| 0.025μ | 62.4 |
| 0.05μ | 69.0 |
| 0.10μ | 68.3 |
| Produced by Sartorius Co. | |
| 0.01μ | Difficult to be filtered |
| 0.05μ | 72.9 |
| 0.10μ | 74.6 |
| Produced by Nuclpore Co. | |
| 0.015μ | Difficult to be filtered |
| 0.03μ | 87.1 |
| 0.05μ | 101.7 |
| 0.08μ | 99.6 |
| Solution prior to filtration through a membrane filter: | 100.0 |

Note: *HGH stands for human growth hormone (the same is to be applied hereinafter).

EXAMPLE 1

1. Experimental materials

| Pore size | Catalogue No. |
|---|---|
| Membrane filters produced by Millipore Co.: | |
| 0.025μ | (VSWP 02500) |
| 0.05μ | (VMWP 02500) |
| 0.10μ | (VCWP 02500) |
| Membrane filters produced by Sartorius Co.: | |
| 0.05μ | (11328) |
| 0.10μ | (11358) |

20% human serum albumin (Chemical & Serum Therapy Research Laboratories (a juridical person), Lot. A 325)

2. Experimental method

As a test solution, there was used 40 ml of the human growth hormone solution. Each filter was fixed onto a filter holder and then autoclaved (at 120° C. for 30 minutes), and the filtration procedure was carried out by use of 5 ml of 0.2% human serum albumin solution (prepared by dilution physiological saline) to perform the coating of the membrane filters.

Subsequently, the filters were washed twice with physiological saline (5 ml×2) to remove excessive human serum albumin, and then the filtration experiment was carried out with 7 ml of the human growth hormone solution.

The human growth hormone was quantitatively determined by radioimmunoassay (RIA Kit manufactured by Dynaboot Co.).

The filtrate of the human growth hormone solution was investigated for contamination of the human growth hromone with human serum albumin by means of SDS-polyacrylamide slab gel electrophoresis.

3. Experimental results

The results are shown in Table 2.

TABLE 2

| Membrane filter | Recovery (%) of HGH* activity in filtrate |
|---|---|
| Produced by Millipore Co. | |
| 0.025μ | 96.3 |
| 0.05μ | 97.0 |
| 0.10μ | 99.8 |
| Produced by Sartorius Co. | |
| 0.05μ | 96.0 |
| 0.10μ | 97.4 |
| Solution prior to filtration through a membrane filter: | 100.0 |

Analysis by SDS-polyacrylamide slab gel electrophoresis indicated that there was no contamination of the HGH solution (filtrate) with human serum albumin.

EXAMPLE 2

1. Experimental materials:
(1) Membrane filter (0.025μ, Cat. No. VSWP 02500) [Millipore Co. Ltd.]
(2) Human growth hormone ["Crorum", Cerono Co. Ltd., Switzerland]
(3) Human serum albumin [Chemo- & Serum-therapy Research Foundation]
(4) Dextran (M.W. 5000-7000) [Nakarai Kagaku Co. Ltd.]
(5) PVP-25 (Polyvinylpyrrolidone 25) [Nakarai Kagaku Co. Ltd.]
(6) L-aginine hydrochloride [Nakarai Kagaku Co. Ltd.]
(7) PEG-4000 (Polyethyleneglycol 4000) [Wako Junyaku Co. Ltd.]
(8) PEG-5000 (Polyethylene-polypropyleneglycol 5000) [Nishio Kagaku Co. Ltd.]
(9) Polygeline (Modified gelatin) [Hochst, Japan]
(10) Human immune globulin [Globelin-I; Nippon Seiyaku Co. Ltd.]
(11) Gelatin (pure powder) [Nakarai Kagaku Co. Ltd.]
(12) MDS (Methyl dextran sulfate) [Kowa Co. Ltd.]
(13) Tween 20 (Polyoxyethylenesorbitan mono-laurate) [Nakarai Kagaku Co. Ltd.]
(14) Tween 80 (Polysorbate 80; Polyoxyethylene sorbitan mono-oleate) [Nakarai Kagaku Co. Ltd.]

2. Experimental method:

Membrane filters were fitted onto respective filter holders of 25 mm in diameter and autoclaved at 120° C. for 30 minutes. Respective 0.5% aqueous solution of materials (3) to (14) were prepared. Each of the membrane filters was pretreated by filtering 5 ml each of the solutions through the filter, thereby the filters were coated with respective materials.

Subsequently, each membrane filter was washed two times with physiological saline (5 ml×2) to remove excess of the coating materials, and then filtration tests were conducted employing 7 ml each of human growth hormone solutions (0.6 IU/ml).

The activity of human growth hormone was assayed with a radioimmunoassay kit (Dainabot Co. Ltd.).

3. Results:

The test results are shown in Table 3.

TABLE 3

| Pretreating solution | Recovery rate (%) of HGH activity in filtrate (HGH activity before filtration = 100%) |
|---|---|
| Physiological saline | 52.6 |
| 0.5% solution of human serum albumin | 98.0 |
| 0.5% solution of dextran | 56.1 |
| 0.5% solution of PVP-25 | 103.0 |
| 0.5% solution of arginine | 54.5 |
| 0.5% solution of PEG-4000 | 51.0 |
| 0.5% solution of | 74.3 |
| 0.5% solution of Polygeline | 88.6 |
| 0.5% solution of human immune globulin | —* |
| 0.5% solution of MDS | 40.1 |
| 0.5% solution of Tweem 20 | 97.0 |
| 0.5% solution of Tween 80 | 94.1 |
| 0.5% solution of gelatin | 93.5 |

*Pretreatment was impossible because of difficulty in filtration.

EXAMPLE 3

1. Experimental materials:
(1) Membrane filter: (0.025μ, Cat. No. USWP 02500) [Millipore Co. Ltd.]
(2) Urokinase (Lot 01016) [Nihon Chemical Research Co. Ltd.]

Materials from (3) Human serum albumin to (13) Tween 80 are the same as those in Example 2.

2. Experimental method:

The membrane filters were fitted onto respective filter holders of 25 mm in diameter and autoclaved at 120° C. for 30 minutes.

Then, the membrane filters were coated with the experimental materials of (3)–(13) respectively, in the same manner as in Example 1, and excessive coating materials were removed by washing with physiologically saline.

Subsequently, filtration tests were conducted employing 7 ml each of urokinase solutions (10,000 IU/ml).

The activity of urokinase was assayed by Fiblin Plate Method (Clin. Chim. Acta 13, 680–684 (1966)).

3. Results:

The results are shown in Table 4.

TABLE 4

| Pretreating solution | Recovery rate (%) of urokinase activity in filtrate (urokinase activity in tested solution = 100%) |
|---|---|
| Physiological saline | 47.7 |
| 0.5% solution of human serum albumin | 90.3 |
| 0.5% solution of dextran | 70.5 |
| 0.5% solution of DVP-25 | 96.4 |
| 0.5% solution of arginine | 49.7 |
| 0.5% solution of PEG-4000 | 65.1 |
| 0.5% solution of PPG-5000 | 66.6 |
| 0.5% solution of Poligeline | 92.3 |
| 0.5% solution of human immune globulin | —* |
| 0.5% solution of MDS | 51.8 |
| 0.5% solution of Tween 20 | 91.0 |
| 0.5% solution of Tween 80 | 90.2 |
| 0.5% solution of gelatin | 93.0 |

*Pretreatment was impossible because of difficulty in filtration.

EXAMPLE 4

1. Experimental materials:
   (1) Human urine kallikrein [Nihon Chemical Research Co., Ltd.]
   (2) Human urine trypsin inhibitor [Nihon Chemical Research Co., Ltd.]
   (3) Human urine epidermal growth factor [Nihon Chemical Research Co., Ltd.]
   (4) Human leucocyte interferon-α [Nihon Chemical Research Co., Ltd.]

2. Experimental method:

With regard to the above materials, experiments were conducted in the same manner as Example 2.

The method for assaying the activities of the above materials are as follows;

Human urine kallikrein: By fluorescent synthetic substrate method (Journal of Biochemistry 82, 1495 (1977)).

Human urine trypsin inhibitor: By the inhibitory activity method of Tanaka et al. (Biochimica et Biophysica Acta 705, 192, (1982)), employing ox trypsin Type I produced by Sigma Co., Ltd.

Human epidermal growth factor: By the enzyme immnoassay method of Hayashi et al. (Biochemistry International 10, 856 (1985)).

Human leukocyte interferon-α: By 50% CPE suppression method employing FL-cell-VSV system ("The interferon System" by W. E. Stewart II, Springer-Verlag).

3. Results:

The results are shown in Table 5.

TABLE 5

| Pretreating solution | Recovery rate (%) of human urine kallikrein (activity before filtration = 100%) | Recovery rate (%) human urine trypsin inhibitor (the same as the left) | Recovery rate (%) human urine epidermal growth hormone (the same as the left) | Recovery rate (%) interferon-α (the same as the left) |
|---|---|---|---|---|
| Physiological saline | 53.4 | 60.3 | 49.0 | 36.4 |
| 0.5% solution of human serum albumin | 95.5 | 99.0 | 91.1 | 96.3 |
| 0.5% solution of dextran | 70.1 | 75.3 | 62.8 | 53.0 |
| 0.5% solution of DVP-25 | 96.3 | 94.4 | 95.3 | 99.2 |
| 0.5% solution of arginine | 51.8 | 60.9 | 55.2 | 45.3 |
| 0.5% solution of PEG-4000 | 70.0 | 76.3 | 56.8 | 58.6 |
| 0.5% solution of PEG-PPG-5000 | 71.3 | 76.6 | 53.3 | 60.5 |
| 0.5% solution of Poligeline | 89.6 | 93.2 | 85.4 | 88.3 |
| 0.5% solution of human immune globulin | —* | —* | —* | —* |
| 0.5% solution of MDS | 46.3 | 60.5 | 51.9 | 36.2 |
| 0.5% solution of Tween 20 | 90.0 | 93.1 | 92.1 | 95.3 |
| 0.5% solution of Tween 80 | 91.4 | 92.1 | 89.3 | 91.4 |
| 0.5% solution of gelatin | 90.2 | 90.3 | 86.7 | 85.6 |

*Pretreating was impossible because of difficulty in filtration.

We claim:

1. A process for recovering from solution at least about 80% of the activity of a physiologically active proteinaceous substance of human origin selected from the group consisting of urokinase, kallikrein, trypsin inhibitor, human epidermal growth factor, human placenta gonadotropin, hypophysis gonadotropin, interferon-α, interferon, superoxide dismutase, plasminogen, antitumor factor of platelet origin and human growth hormone, which process comprises filtering said solution containing the active proteinaceous substance through a membrane filter of 0.025 to 0.05μ in pore size to remove a virus which may be present in said proteinaceous substance, the membrane filter being previously treated with a 0.2 to 0.5% solution of a water-soluble high molecular substance selected from the group consisting of human serum albumin, polyvinylpyrrolidone, polyoxyethylene sorbitan mono-laurate, polysorbate 80 and modified or unmodified gelatin.

2. A process according to claim 1 wherein the solution of a water-soluble high molecular substance is an aqueous solution containing the water-soluble substance in a concentration from 0.2 to 0.5%.

3. A process according to claim 1 wherein the previous treatment of the membrane filter is carried out by passing the solution of a water-soluble high molecular substance through the filter.

* * * * *